(12) United States Patent
Richard et al.

(10) Patent No.: US 7,914,805 B2
(45) Date of Patent: Mar. 29, 2011

(54) IMPLANTABLE OR INSERTABLE MEDICAL DEVICES CONTAINING RADIATION-TREATED POLYMER FOR IMPROVED DELIVERY OF THERAPEUTIC AGENT

(75) Inventors: Robert E. Richard, Wrentham, MA (US); Marlene C. Schwarz, Aurburndale, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1572 days.

(21) Appl. No.: 10/632,054

(22) Filed: Jul. 31, 2003

(65) Prior Publication Data
US 2005/0025801 A1 Feb. 3, 2005

(51) Int. Cl.
*A61F 13/00* (2006.01)
*A61F 2/00* (2006.01)
*A61K 9/70* (2006.01)
*A61K 9/14* (2006.01)

(52) U.S. Cl. ........ 424/422; 424/423; 424/443; 424/484; 424/486

(58) Field of Classification Search .................. 424/422, 424/423, 443, 484, 486
See application file for complete search history.

(56) References Cited

U.S. PATENT DOCUMENTS

| | | | |
|---|---|---|---|
| 4,946,899 A | 8/1990 | Kennedy et al. | 525/244 |
| 5,163,952 A | 11/1992 | Froix | 623/1 |
| 5,258,020 A | 11/1993 | Froix | 623/1 |
| 5,304,121 A | 4/1994 | Sahatjian | 604/53 |
| 5,571,166 A * | 11/1996 | Dinh et al. | 128/898 |
| 5,616,608 A | 4/1997 | Kinsella et al. | 514/449 |
| 5,674,242 A * | 10/1997 | Phan et al. | 606/198 |
| 5,716,981 A | 2/1998 | Hunter et al. | 514/449 |
| 5,733,925 A | 3/1998 | Kunz et al. | 514/449 |
| 5,741,331 A | 4/1998 | Pinchuk | 623/11 |
| 5,789,018 A | 8/1998 | Engelson et al. | 427/2.3 |
| 5,871,437 A | 2/1999 | Alt | 600/3 |
| 5,879,697 A | 3/1999 | Ding et al. | 424/422 |
| 5,954,706 A | 9/1999 | Sahatjian | 604/509 |
| 6,099,562 A | 8/2000 | Ding et al. | 623/1.46 |
| 6,159,142 A | 12/2000 | Alt | 600/3 |
| 6,280,411 B1 | 8/2001 | Lennox | |
| 6,335,029 B1 | 1/2002 | Kamath et al. | 424/423 |
| 6,426,339 B1 * | 7/2002 | Berde et al. | 514/180 |
| 6,537,569 B2 * | 3/2003 | Cruise | 424/426 |
| 6,545,097 B2 | 4/2003 | Pinchuk et al. | 525/240 |
| 2002/0099438 A1 * | 7/2002 | Furst | 623/1.16 |
| 2002/0107330 A1 * | 8/2002 | Pinchuk et al. | 525/242 |
| 2002/0197296 A1 | 12/2002 | Gen | 424/423 |
| 2003/0224033 A1 * | 12/2003 | Li et al. | 424/423 |

FOREIGN PATENT DOCUMENTS

| | | |
|---|---|---|
| EP | 0879595 A2 | 11/1998 |
| WO | WO 96/03147 | 2/1996 |
| WO | WO 97/10011 | 3/1997 |
| WO | WO 00/59516 | 10/2000 |
| WO | WO 02/47731 A2 | 6/2002 |

OTHER PUBLICATIONS

Rosiak, J.M., et al., "Drug Delivery System for the Treatment of Endometrial Carcinoma," *Radiation Physics and Chemistry.*, vol. 52, No. 1-6, Jun. 1998, pp. 307-311.
Reference: Polymer Properties. Thermal Transitions of Homopolymers: Glass Transition & Melting Point. http://www.sigmaaldrich.com/img/assets/3900/Thermal_Transitions_of_Homopolymers.pdf.
Services: Crosslinking. http://www.webmpi.com/cross.html.
Physique & industrie—Radiation processing. Physique & industrie research under contract. Compact Electrostatic Accelerators. http://www.physiqueindustrie.com/_cea.htm.
Radiation Processing of Polymer. Radiation Processing in Your Life. http://www.geocities.com/msen20/Radprocessingofpolymers.pdf.
Karl J. Hemmerich. Polymer Materials Selection for Radiation-Sterilized Products. http://www.devicelink.com/mddi/archive/00/02/006.html.

* cited by examiner

*Primary Examiner* — Raymond J Henley, III
(74) *Attorney, Agent, or Firm* — Mayer & Williams PC; David B. Bonham; Keum J. Park

(57) ABSTRACT

An implantable or insertable medical device which comprises (a) a therapeutic agent and (b) a polymeric release region comprising a polymer. The polymeric release region is treated with a radiation dose that is effective to substantially increase the cumulative release of the therapeutic agent subsequent to administration to a patient. The polymeric release region can be, for example, (a) a carrier region that comprises the therapeutic agent or (b) a barrier region that is disposed over a therapeutic-agent-containing region that comprises the therapeutic agent. The present invention is further directed to methods of forming such medical devices, methods of releasing a therapeutic agent within a patient using such medical devices, and methods of modulating the release of a therapeutic agent from such medical devices.

28 Claims, 2 Drawing Sheets

US 7,914,805 B2

IMPLANTABLE OR INSERTABLE MEDICAL DEVICES CONTAINING RADIATION-TREATED POLYMER FOR IMPROVED DELIVERY OF THERAPEUTIC AGENT

FIELD OF THE INVENTION

The present invention relates to implantable or insertable medical devices for delivery of one or more therapeutic agents.

BACKGROUND OF THE INVENTION

Numerous medical devices have been developed for the delivery of therapeutic agents to the body. In accordance with some delivery strategies, a therapeutic agent is provided (a) within a polymeric carrier layer and/or (b) beneath a polymeric barrier layer that is associated with an implantable or insertable medical device. Once the medical device is placed at the desired location within a patient, the therapeutic agent is released from the medical device at a rate that is dependent upon the nature of the polymeric carrier and/or barrier layer.

The desired release profile for the therapeutic agent is dependent upon the particular treatment at hand, including the specific condition being treated, the specific therapeutic agent selected, the specific site of administration, and so forth. As a result, there is a continuing need for polymeric layers, including polymeric barrier layers and carrier layers, which are able to provide a range of therapeutic agent release rates.

SUMMARY OF THE INVENTION

The present invention is directed to novel implantable or insertable medical devices, which provide release of a therapeutic agent.

According to a first aspect of the present invention, an implantable or insertable medical device is provided, which comprises (a) a therapeutic agent and (b) a polymeric release region. The polymeric release region is treated with a radiation dose effective to substantially increase the cumulative release of the therapeutic agent subsequent to administration to a patient.

For example, the cumulative release of therapeutic agent may be increased by an amount selected from 10% or more, 20% or more, 25% or more, 35% or more, 50% or more, 100% or more, 200% or more, 400% or more, or 1000% or more, after a period of administration selected from 1 day, 2 days, 4 days, 1 week, 2 weeks, 4 weeks, 2 months, 6 months and 1 year.

The polymeric release region can be, for example, (a) a carrier region that comprises the therapeutic agent or (b) a barrier region that is disposed over a therapeutic-agent-containing region that comprises the therapeutic agent.

In some embodiments of the invention, the polymeric release region comprises a polymer, which further comprises a plurality of ($-CH_2-CR_1R_2-$)$_n$ groups within a polymer chain, where $R_1$ and $R_2$ are organic radicals independently selected from $C_1$-$C_{20}$ alkyl, $C_2$-$C_{20}$ alkoxyalkyl, and $C_3$-$C_{20}$ alkylcarboxylic ester. For example, the polymer can comprise poly(methyl methacrylate) and/or polyisobutylene chains. As a more specific example, the polymer can be a copolymer comprising polyisobutylene and polystyrene regions, such as a polystyrene-polyisobutylene-polystyrene triblock copolymer.

According to another aspect of the present invention, a method of forming an implantable or insertable medical device like those described herein is provided, which comprises: (a) applying a coating comprising a polymer on a surface of an implantable or insertable medical device; and (b) exposing the coating to a dose of radiation that is effective to substantially increase the cumulative release of the therapeutic agent subsequent to administration to a patient.

For example, the radiation dose is typically 100,000 rads or more, more typically 1 Mrad or more, for example, ranging from 1 Mrad to 20 Mrad.

The radiation dose can be provided using a variety of radiation types, including gamma ray radiation and electron beam radiation.

According to another aspect of the invention, the rate of release of the therapeutic agent from the medical device is modulated by modifying the radiation dose that is applied to the medical device. For example, using the approach described here, a desired drug release can be "dialed in" for a prefabricated medical device.

According to yet another aspect of the invention, a method of releasing a therapeutic agent within a patient is provided, which comprises: (a) providing an implantable or insertable medical device like those described herein, and (b) implanting or inserting the implantable or insertable medical device into a patient. For example, the medical device may be implanted or inserted into the coronary vasculature, peripheral vascular system, esophagus, trachea, colon, biliary tract, urinary tract, prostate or brain of the patient. As a more specific example, the medical device may be inserted into the vasculature of the patient, for example, to release a therapeutic agent for the treatment of restenosis.

One advantage of the present invention is that implantable or insertable medical devices can be provided, which provide for controlled release of a therapeutic agent.

Another advantage of the present invention is that such devices can be provided using radiation-based techniques, which are clean and inexpensive.

Another advantage of the present invention is that the drug release profile associated with such devices can be altered by modifying the dosage of the radiation that is applied, avoiding the need to reformulate the chemical composition of the polymeric release region. In this way, the therapeutic agent release profile can be modified, even after the device is fabricated. For example, one can produce slow, medium and fast release devices from a single batch of prefabricated devices by subjecting sub-lots of the batch to differing amounts of radiation.

These and other embodiments and advantages of the present invention will become immediately apparent to those of ordinary skill in the art upon review of the Detailed Description and Claims to follow.

DETAILED DESCRIPTION OF THE INVENTION

Figure 1A:
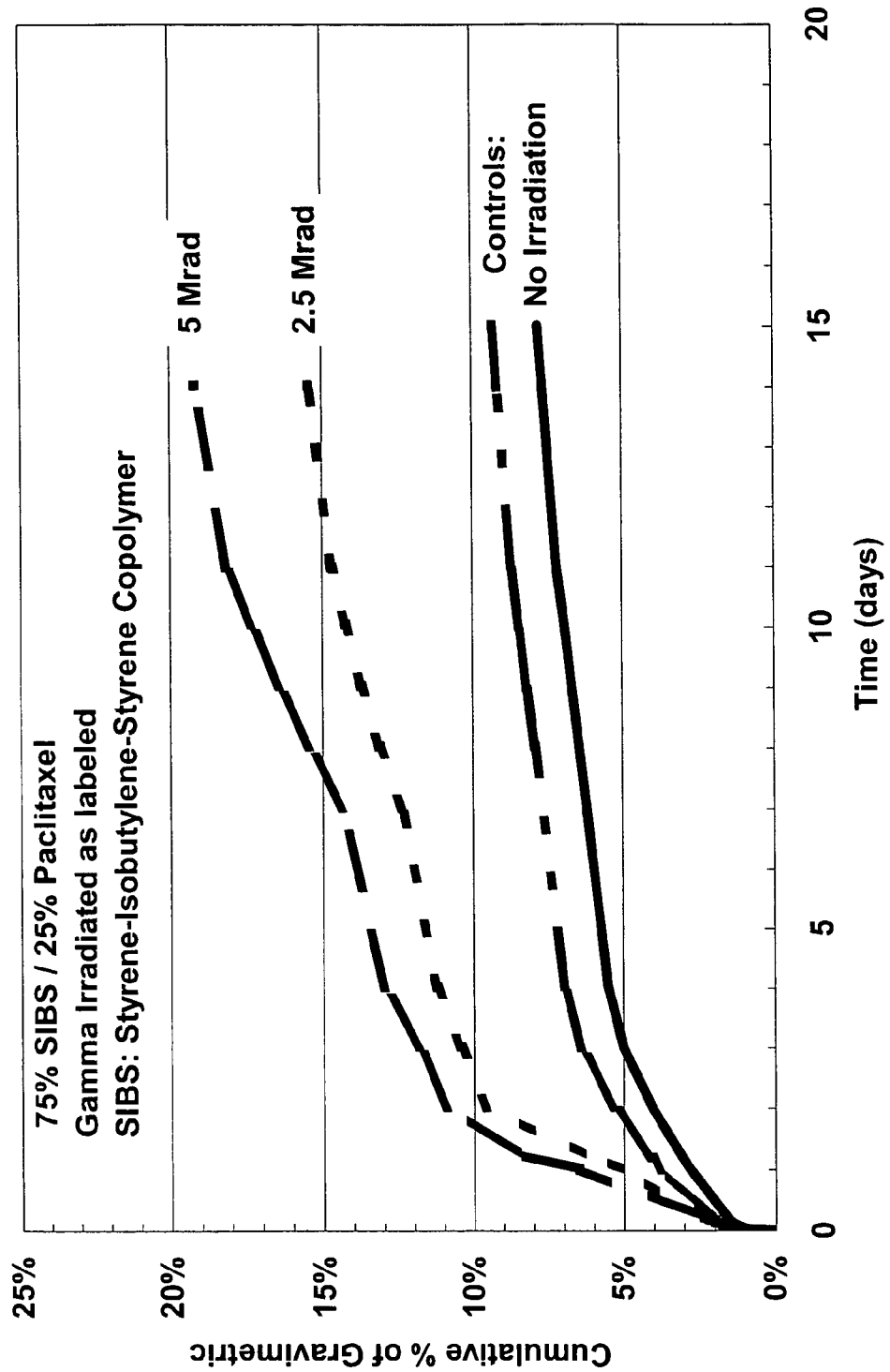
FIGS. 1A and 1B illustrate cumulative release of paclitaxel as a function of time for stents coated with a layer containing polystyrene-polyisobutylene-polystyrene block copolymer and paclitaxel, for various radiation dosages.

According to one aspect of the present invention, an implantable or insertable medical device is provided, which comprises (a) a therapeutic agent and (b) a polymeric release region, which further comprises a polymer. The release region is treated with a radiation dose that is effective to substantially increase the cumulative release of the therapeutic agent subsequent to administration to a patient.

By "polymeric release region" is meant a region, which contains a polymer and which regulates the rate of release of a therapeutic agent. Release regions are commonly either carrier regions or barrier regions. A "carrier region" is region which contains at least one therapeutic agent and from which the therapeutic agent is released. A "barrier region" is a region that is disposed between a source of therapeutic agent and a site of intended release and which controls the rate at which the therapeutic agent is released.

The polymeric release region can be present in the medical device in a number of configurations. For example, the polymeric release region can constitute the entirety of the medical device, or it can constitute only a portion of the medical device. The portion of the medical device can be, for example, (a) one or more medical device layers (e.g., one or more coating layers), (b) one or medical device components or portions thereof, and so forth.

For example, in some embodiments of the present invention, an outer carrier layer is disposed over at least a portion of an implantable or insertable medical device. Upon implantation or insertion of the device into a patient, the therapeutic agent is released from the carrier layer in a controlled fashion. In other embodiments, a therapeutic-agent-containing layer is disposed over at least a portion of an implantable or insertable medical device. A barrier layer is disposed over the therapeutic-agent-containing layer. As a result, the barrier layer acts to control release of the therapeutic agent from the medical device upon implantation or insertion of the same.

Preferred implantable or insertable medical devices for use in conjunction with the present invention include catheters (for example, renal or vascular catheters such as balloon catheters), guide wires, balloons, filters (e.g., vena cava filters), stents (including coronary vascular stents, cerebral, urethral, ureteral, biliary, tracheal, gastrointestinal and esophageal stents), stent grafts, cerebral aneurysm filler coils (including Guglilmi detachable coils and metal coils), vascular grafts, myocardial plugs, patches, pacemakers and pacemaker leads, heart valves, biopsy devices, or any coated substrate (which can comprise, for example, glass, metal, polymer, ceramic and combinations thereof) that is implanted or inserted into the body, either for procedural use or as an implant, and from which therapeutic agent is released.

The medical devices contemplated for use in connection with the present invention include drug delivery medical devices that are used for either systemic treatment or for the localized treatment of any mammalian tissue or organ. Non-limiting examples are tumors; organs including but not limited to the heart, coronary and peripheral vascular system (referred to overall as "the vasculature"), lungs, trachea, esophagus, brain, liver, kidney, bladder, urethra and ureters, eye, intestines, stomach, pancreas, ovary, and prostate; skeletal muscle; smooth muscle; breast; cartilage; and bone.

One particularly preferred medical device for use in connection with the present invention is a vascular stent that delivers therapeutic agent into the vasculature for the treatment of restenosis. As used herein, "treatment" refers to the prevention of a disease or condition, the reduction or elimination of symptoms associated with a disease or condition, or the substantial or complete elimination a disease or condition. Preferred subjects (also referred to as patients) are vertebrate subjects, more preferably mammalian subjects and more preferably human subjects.

As noted above, the implantable or insertable medical devices of the present invention are treated with a radiation dose that is effective to substantially increase the cumulative release of the therapeutic agent subsequent to administration of the device. By "substantial increase" is meant that an increase of at least 10%.

Although the release characteristics that are ultimately of interest are the release characteristics subsequent to implantation or insertion (administration) to a subject, it is well known in the art to quantify release characteristics of a medical device within an experimental system, which gives an indication of the actual release characteristics within the subject. For example, aqueous buffer systems are commonly used for testing release of therapeutic agents from vascular devices. Hence, whether or not a radiation dose is effective to substantially increase the cumulative release of the therapeutic agent subsequent to administration of the device to a patient can generally be determined by measuring the cumulative release of therapeutic agent in an experimental system, such as an aqueous buffer solution.

Examples of substantial increases in cumulative release (relative to a non-irradiated device) include cumulative release increases of at least 10%, at least 20%, at least 25%, at least 35%, at least 50%, at least 100%, at least 200%, at least 500%, at least 1000%, or more, after 1 day, 2 days, 4 days, 1 week, 2 weeks, 4 weeks, 3 months, 6 months or 1 year of being implanted or inserted in a patient (or placed in a surrogate experimental system).

Without wishing to be bound by theory, when polymers are exposed to radiation, at least two basic reactions are believed to occur: (1) chain scission (i.e., a random rupturing of bonds) of polymer molecules and (2) cross-linking of polymer molecules. Crosslinking generally results in the formation of larger, three-dimensional polymer structures. Chain scission, on the other hand, generally results in a decrease in the molecular weight of the polymer molecules. While polymers may display both types of reactions, one type of reaction will typically dominate. For increased release, it is preferred to use polymers in which chain scission reactions dominate. Chain scission is generally evidenced by a reduction in the molecular weight of the polymer (e.g., the weight-average or number-average molecular weight of the polymer) upon exposure to the radiation.

So long as it is of sufficiently high energy, essentially any type of radiation can be used in connection with the present invention. Preferred sources of high-energy radiation include gamma rays, X rays, and electron beams. Typically, the radiation-treated polymeric release region is exposed to a radiation dose of between 10,000 rads and 100 Mrad. This includes, for example, 10,000 rads, 100,000 rads, 500,000 rads, 1,000,000 rads (1 Mrad), 2.5 Mrad, 5 Mrad, 7.5 Mrad, 10 Mrad, 20 Mrad, 50 Mrad and 100 Mrad, as well as ranges between any two of these doses, for example, 10,000 rad to 500,00 rad, 10 Mrad to 20 Mrad, and so forth, with 1 Mrad to 10 Mrad being preferred in some embodiments.

As noted above, radiation treatment is clean and inexpensive. Moreover, the release characteristics of the medical device can be changed by merely modifying the dose of the radiation that is applied. As a result, the release characteristics can be set, even after the device is fabricated.

The radiation dosages used in connection with the present invention are sufficiently high to sterilize the medical device in some embodiments. This is advantageous for therapeutic agents that are not compatible with ethylene oxide or other modes of sterilization that involve the application of heat, moisture and/or reactive chemicals.

A wide variety of polymers are available for use in release regions of implantable or insertable medical devices, including one or more of the following: polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydoxyalkyl celluloses; polyoxymethylene polymers and copolymers; polyimide polymers and copolymers such as polyether block imides, polyamidimides, polyesterimides, and polyetherimides; polysulfone polymers and copolymers including polyarylsulfones and polyethersulfones; polyamide polymers and copolymers including nylon 6,6, polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, polystyrenes, styrene-maleic anhydride copolymers, styrene-butadiene copolymers, styrene-ethylene-butylene copolymers (e.g., a polystyrene-polyethylene/butylene-polystyrene (SEBS) copolymer, available as Kraton® G series polymers), acrylonitrile-styrene copolymers, acrylonitrile-butadiene-styrene copolymers, styrene-butadiene copolymers and styrene-isobutylene copolymers (e.g., polyisobutylene-polystyrene block copolymers such as SIBS), polyvinyl ketones, polyvinylcarbazoles, and polyvinyl esters such as polyvinyl acetates; polybenzimidazoles; ionomers; polyalkyl oxide polymers and copolymers including polyethylene oxides (PEO); glycosaminoglycans; polyesters including polyethylene terephthalates and aliphatic polyesters such as polymers and copolymers of lactide (which includes lactic acid as well as d-,l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of polylactic acid and polycaprolactone is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; polyurethanes; p-xylylene polymers; polyiminocarbonates; copoly(ether-esters)such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as blends and copolymers of the above.

These polymers may be provided in a variety of configurations, including cyclic, linear and branched configurations. Branched configurations include star-shaped configurations (e.g., configurations in which three or more chains emanate from a single branch point), comb configurations (e.g., graft polymers having a main chain and a plurality of branching side chains), and dendritic configurations (including arborescent or hyperbranched polymers). As noted above, they can be formed from a single monomer (i.e., they can be homopolymers), or they can be formed from multiple monomers (i.e., they can be copolymers), which can be distributed, for example, randomly, in an orderly fashion (e.g., in an alternating fashion), or in blocks. Typically, the polymers used in connection with the present invention will be formed from 10 or more monomers, more typically 50, 100, 500, 1000, 10000, or even more monomers.

At least one of the polymers in the polymeric release region is sufficiently radiation sensitive such that a substantial increase in cumulative release occurs upon exposure to radiation. One skilled in the art can readily determine whether a polymer provides such an increase in cumulative release upon radiation exposure.

Preferred radiation-sensitive polymers for the practice of the invention include, for example, homopolymers and copolymers containing polytetrafluoroethylene, collagen, cellulose, poly(methyl-methacrylate), polyisobutylene, poly (2-methyl butene), poly(2-methyl pentene), and other polymeric blocks having alternating quaternary and secondary carbons, e.g., $(-CH_2-CR_1R_2-)_n$, where n is an integer, and $R_1$ and $R_2$ are organic radicals, for example, $C_1$-$C_{10}$ alkyl (which, as used herein, can be liner or branched, substituted or unsubstituted), $C_2$-$C_{20}$ alkoxyalkyl, $C_3$-$C_{20}$ alkylcarboxylic ester, and so forth.

In some embodiments, a number of radiation sensitive groups are distributed within the polymer in either a random or a predefined manner to program the breakdown of the molecular weight of the polymer. These groups represent "weak links" in the polymer chain, corresponding to expected scission points when the polymer chain is exposed to a specific dose of radiation. By coupling such radiation sensitive groups between polymer segments that are more radiation stable, the lower limit of molecular weight degradation can be effectively controlled.

Copolymers containing polyisobutylene and polystyrene, including diblock copolymers, triblock copolymer, star block copolymers, graft copolymers, dendrimers, and so forth, are one beneficial family of polymers for the practice of the present invention. Several polymers within this family, including polystyrene-polyisobutylene-polystyrene triblock copolymers (SIBS copolymers), are described in U.S. patent application 20020107330 entitled "Drug delivery compositions and medical devices containing block copolymer."

Prior to radiation exposure, the device or device portion to which the polymeric release region corresponds (for example, a device coating, a device component, or an entire device) can be formed using a number of known techniques.

For example, where the polymer components of the polymeric release region have thermoplastic characteristics, a variety of standard thermoplastic processing techniques can be used to form the polymeric release region, including compression molding, injection molding, blow molding, spinning, vacuum forming and calendaring, as well as extrusion into sheets, fibers, rods, tubes and other cross-sectional profiles of various lengths.

As one specific example, an entire stent structure can be extruded using the above techniques. As another example, a coating can be provided by extruding a coating layer onto a pre-existing stent. As yet another example, a coating can be co-extruded along with an underlying stent structure.

If the therapeutic agent is also stable under processing conditions, then it can be combined with the polymer prior to thermoplastic processing to produce a therapeutic-agent-containing carrier region. If not, then a therapeutic-agent-containing carrier region can be formed by post-processing introduction of therapeutic agent as discussed below.

In other embodiments, the polymeric release region is formed using solvent-based techniques in which components of the polymeric release region are first dissolved in a solvent system that contains one or more solvent species, and the resulting mixture is subsequently used to form a polymeric region.

The solvent system that is selected is preferably a good solvent for the component(s) of the polymeric region and, where included, for the therapeutic agent as well. The particular solvent system may also be selected based on other characteristics including drying rate and surface tension. The polymer can also be dispersed in a non-solvent as a dispersion or emulsion prior to being applied.

Preferred solvent-based techniques include, but are not limited to, solvent casting techniques, spin coating techniques, web coating techniques, solvent spraying techniques, dipping techniques, techniques involving coating via mechanical suspension such as air suspension, ink jet techniques, electrostatic techniques, and combinations of these processes.

Where solvent-based processing is employed, a mixture containing the solvent(s) and the component(s) of the polymeric release region (e.g., a polymer such as SIBS) are preferably applied to a substrate to form the release region.

In some embodiments, the substrate is all or a portion of an implantable or insertable medical device to which the polymeric region is applied. In other embodiments, the substrate is a template from which the polymeric region is removed after solvent elimination. Such template-based techniques are particularly appropriate for forming simple objects such as sheets, tubes, cylinders and so forth, which can be easily removed from a template substrate. In other techniques, for example, fiber forming techniques, the polymeric region is formed without the aid of a substrate or template.

Where appropriate, techniques such as those listed above can be repeated or combined to build up a polymeric region to a desired thickness. The thickness of the polymeric region can be varied in other ways as well. For example, in solvent spraying, thickness can be increased by modification of coating process parameters, including increasing spray flow rate, slowing the movement between the substrate to be coated and the spray nozzle, providing repeated passes and so forth.

Where a carrier region is formed (as opposed to, for example, a barrier region), a therapeutic agent can be included in the mixture containing the solvent(s) and polymer (s) and hence co-established with the carrier region. In other embodiments, the therapeutic agent is introduced into a previously formed polymeric region. For example, the therapeutic agent can be dissolved within a solvent, and the resulting solution contacted with the previously formed polymeric region using, for example, one or more of the application techniques described above (e.g., dipping, spraying, etc.).

As previously noted, barrier layers can be formed over a therapeutic-agent-containing region. In some embodiments, the therapeutic-agent-containing region will comprise one or more polymers, which can be selected, for example, from the polymers described elsewhere in this application. In these instances, the therapeutic-agent-containing region can be established, for example, using the solvent-based techniques (e.g., dipping, spraying, etc.) that are discussed above. In other embodiments, the therapeutic-agent-containing region beneath the barrier layer is established without an associated polymer. In this case, the therapeutic agent can simply be dissolved or dispersed in a solvent or liquid, and the resulting solution/dispersion can be applied to a substrate again using, for example, one or more of the application techniques described above (e.g., dipping, spraying, etc.).

Where a polymeric release region is formed using a solvent-based technique, it is preferably dried after application to remove the solvents. Where the polymeric release region is a release layer coated on an underlying medical device, the release layer typically further conforms to the underlying medical device during the drying process.

"Therapeutic agents", "pharmaceutically active agents", "pharmaceutically active materials", "drugs" and other related terms may be used interchangeably herein and include genetic therapeutic agents, non-genetic therapeutic agents and cells. Therapeutic agents may be used singly or in combination. Therapeutic agents may be, for example, nonionic or they may be anionic and/or cationic in nature.

Exemplary non-genetic therapeutic agents for use in connection with the present invention include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) anti-neoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; and (o)agents that interfere with endogenous vasoactive mechanisms.

Exemplary genetic therapeutic agents for use in connection with the present invention include anti-sense DNA and RNA as well as DNA coding for: (a) anti-sense RNA, (b) tRNA or rRNA to replace defective or deficient endogenous molecules, (c) angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP- 12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include (a) plasmids, (b) viral vectors such as adenovirus, adenoassociated virus and lentivirus, and (c) non-viral vectors such as lipids, liposomes and cationic lipids.

Cells for use in connection with the present invention include cells of human origin (autologous or allogeneic), including stem cells, or from an animal source (xenogeneic), which can be genetically engineered, if desired, to deliver proteins of interest.

Numerous therapeutic agents, not necessarily exclusive of those listed above, have been identified as candidates for vascular treatment regimens, for example, as agents targeting restenosis. Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including $\alpha$-antagonists such as prazosin and bunazosine, $\beta$-antagonists such as propranolol and $\alpha/\beta$-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) ACE inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and $\beta$-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-$\beta$ pathway agents such as polyanionic agents (heparin, fucoidin), decorin, and TGF-$\beta$ antibodies, EGF pathway agents such as EGF antibodies, receptor antagonists and chimeric fusion proteins, TNF-$\alpha$ pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Numerous additional therapeutic agents useful for the practice of the present invention are also disclosed in U.S. Pat. No. 5,733,925 assigned to NeoRx Corporation, the entire disclosure of which is incorporated by reference.

A wide range of therapeutic agent loadings can be used in connection with the medical devices of the present invention, with the amount of loading being readily determined by those of ordinary skill in the art and ultimately depending, for example, upon the condition to be treated, the nature of the therapeutic agent itself, the means by which the therapeutic agent is administered to the intended subject, and so forth.

In addition to radiation exposure, the release characteristics associated with the release layers of the present invention can be influenced in a number of ways including the following: (a) varying the type, molecular weight and/or relative amount of the radiation sensitive polymer(s) within the polymeric release region, (b) providing one or more polymers within the release region in addition to the radiation-sensitive polymer(s), (c) varying the porosity of the polymeric release region, and (d) where solvent-based techniques are used to form the polymeric release region, varying the type and relative amounts of solvents used in processing the polymeric release region. The release of therapeutic agent can also be controlled, for example, by varying the thickness of the polymeric release region. Moreover, multiple polymeric release regions can be employed to achieve this end. In addition, where a carrier region is employed, a therapeutic-agent concentration gradient can be established within the carrier region to control release of therapeutic agent.

The invention is further described with reference to the following non-limiting Example.

EXAMPLE

A solution is provided that contains (a) 25 wt % tetrahydrofuran (THF), (b) 74 wt % toluene, (c) 0.25 wt % paclitaxel and (d) 0.75 wt % SIBS copolymer. The solution is prepared by (1) mixing the paclitaxel and tetrahydrofuran, (2) adding the polymer, (3) adding the toluene, (4) thoroughly mixing (e.g., overnight), and (5) filtering.

The solution is then placed in a syringe pump and fed to a spray nozzle. A stent is mounted onto a holding device parallel to the nozzle and rotated to ensure uniform coverage. Depending on the spray equipment used, either the stent or spray nozzle can be moved while spraying, such that the nozzle moves along the component while spraying for one or more passes. After a carrier coating is formed in this fashion, the stent is dried, for example, by placing it in a preheated oven. A portion of the stents formed in this manner are used as controls (i.e., no irradiation), while other portions are subjected to 2.5 Mrad, 5 Mrad and 7.5 Mrad doses of treating radiation.

Figure 1B:
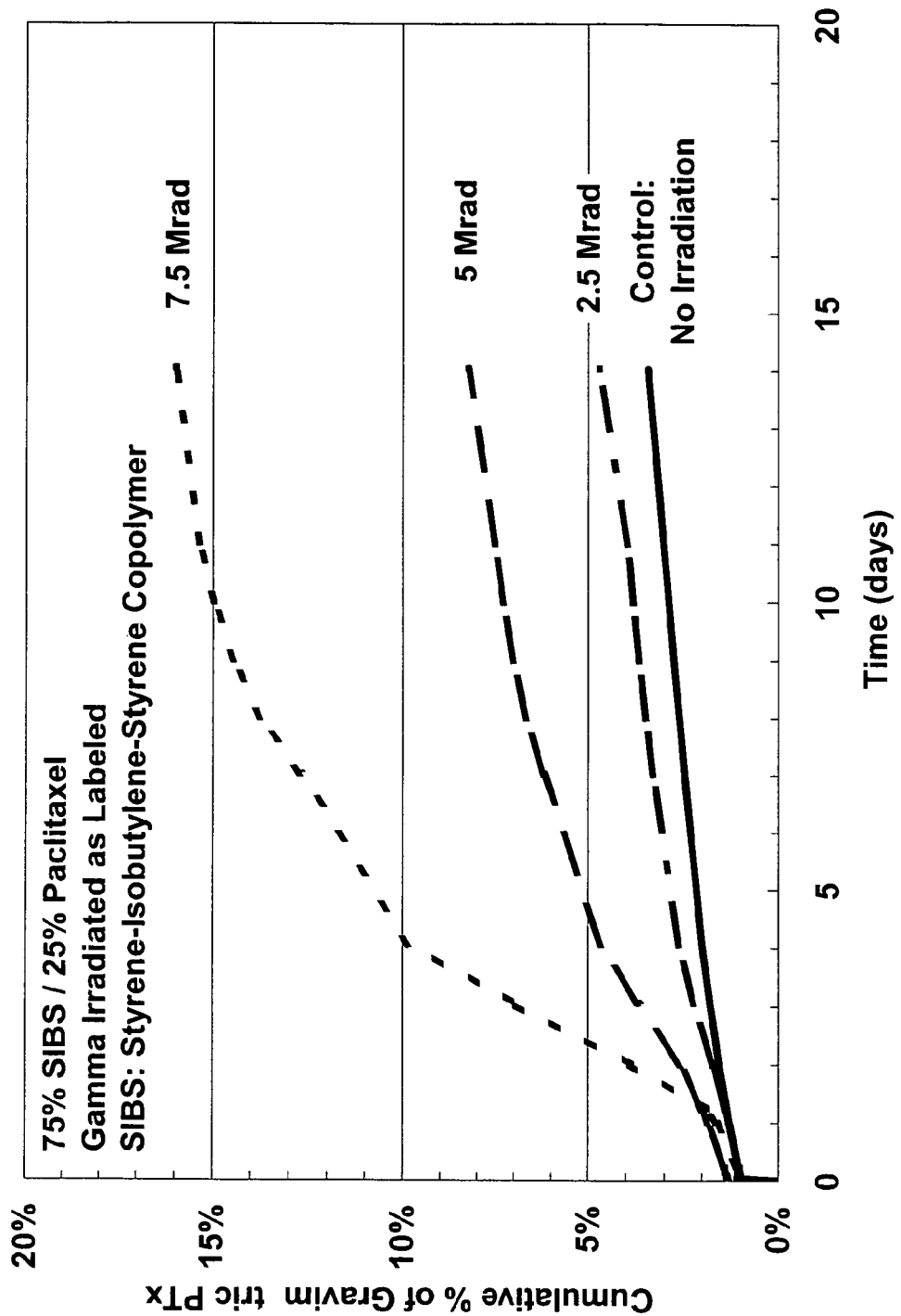

Paclitaxel release is then measured as a function of time in PBS with 0.5 wt % Tween® 20 (polyoxyethylene(20) sorbitan monolaurate), available from Sigma-Aldrich. The results, presented as the cumulative release of paclitaxel as a function of time, are graphically illustrated in FIGS. 1A and 1B for different lots of SIBS, with an average of three stents for each line.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. An implantable or insertable medical device comprising (a) a therapeutic agent and (b) a polymeric release region further comprising a polymer selected from the group consisting of homopolymers and copolymers comprising polytetrafluoroethylene, collagen, cellulose, polyisobutylene, poly(2-methyl butane), or poly(2-methyl pentene) which comprise radiation sensitive groups, wherein said polymeric release region is treated with a radiation dose of at least 100,000 rads that is effective to (i) reduce the molecular weight of the polymer and (ii) substantially increase the cumulative release of said therapeutic agent in an amount of at least 10% subsequent to administration to a patient.

2. The implantable or insertable medical device of claim 1, wherein said polymeric release region is treated with a radiation dose of at least 1,000,000 rads.

3. The implantable or insertable medical device of claim 1, wherein said polymeric release region is a carrier region that comprises said therapeutic agent.

4. The implantable or insertable medical device of claim 1, wherein said polymeric release region is a barrier region disposed over a therapeutic-agent-containing region that comprises said therapeutic agent.

5. The implantable or insertable medical device of claim 1, wherein said polymeric release region is in the form of a coating layer.

6. The implantable or insertable medical device of claim 1, wherein said implantable or insertable medical device is selected from the group consisting of a catheter, a guide wire, a balloon, a filter, a stent, a stent graft, a vascular graft, a vascular patch, and a shunt.

7. The implantable or insertable medical device of claim 1, wherein said implantable or insertable medical device is adapted for implantation or insertion into the coronary vasculature, peripheral vascular system, esophagus, trachea, colon, biliary tract, urinary tract, prostate or brain.

8. The implantable or insertable medical device of claim 1, wherein said therapeutic agent is selected from one or more of the group consisting of an anti-thrombotic agent, an anti-proliferative agent, an anti-inflammatory agent, an anti-migratory agent, an agent affecting extracellular matrix production and organization, an anti-neoplastic agent, an anti-mitotic agent, an anesthetic agent, an anti-coagulant, a vascular cell growth promoter, a vascular cell growth inhibitor, a cholesterol-lowering agent, a vasodilating agent, and an agent that interferes with endogenous vasoactive mechanisms.

9. The implantable or insertable medical device of claim 1, wherein the cumulative release of therapeutic agent is increased by an amount selected from 15% or more, 25% or more, 35% or more, 50% or more, 100% or more, and 200% or more, 400% or more, or 1000% or more, after a period of administration selected from 1 day, 2 days, 4 days, 1 week, 2 weeks, 4 weeks, 2 months, 6 months and 1 year.

10. The implantable or insertable medical device of claim 1, wherein the cumulative release of therapeutic agent is increased by an amount ranging from 25% to 1000%, after a period of administration selected from 1 day, 2 days, 4 days, 1 week, 2 weeks, 4 weeks, 2 months, 6 months and 1 year.

11. The implantable or insertable medical device of claim 1, wherein said polymer comprises polyisobutylene, and wherein said cumulative release of therapeutic agent is increased by an amount ranging from 25% to 1000% after a period of administration selected from 3.5 days, 1 week, and 2 weeks.

12. The implantable or insertable medical device of claim 1, wherein said polymer comprises polyisobutylene and polystyrene, and wherein said cumulative release of therapeutic agent is increased between 100% and 1000% after 1 week of administration.

13. The implantable or insertable medical device of claim 1, wherein said polymer comprises poly(methyl methacrylate).

14. The implantable or insertable medical device of claim 1, wherein said polymer comprises polyisobutylene.

15. The implantable or insertable medical device of claim 14, wherein said polymer comprises polyisobutylene and polystyrene.

16. The implantable or insertable medical device of claim 15, wherein said polymer is a polystyrene-polyisobutylene-polystyrene triblock copolymer.

17. A method of forming the implantable or insertable medical device of claim 1, comprising: (a) applying a coating comprising said polymer on a surface of an implantable or insertable medical device; and (b) exposing said coating to a radiation dose that is effective to substantially increase the cumulative release of said therapeutic agent subsequent to administration to a patient.

18. The method of claim 17, wherein said radiation dose is at least 100,000 rads.

19. The method of claim 17, wherein said radiation dose is at least 1,000,000 rads.

20. The method of claim 17, wherein said radiation dose is provided by gamma ray or electron beam radiation.

21. The method of claim 17, wherein said coating is applied over a therapeutic-agent-containing region that comprises said therapeutic agent.

22. A method of releasing a therapeutic agent within a patient comprising (a) providing the implantable or insertable medical device of claim 1 and (b) implanting or inserting the implantable or insertable medical device into a patient.

23. The method of claim 22, wherein said medical device is selected from a catheter, a guide wire, a balloon, a filter, a stent, a stent graft, a vascular graft, a vascular patch, and a shunt.

24. The method of claim 23, wherein said medical device is inserted into the vasculature.

25. The method of claim 24, wherein said therapeutic agent is released in the treatment of restenosis.

26. A method for providing first and second implantable or insertable medical devices having first and second release profiles comprising: (a) providing first and second implantable or insertable medical devices comprising a therapeutic agent and a polymeric release region that further comprises a polymer, and (b) exposing said first medical device to a first radiation dose that is effective to provide a first substantial increase in the cumulative release of said therapeutic agent subsequent to administration to a patient, and (c) exposing said second medical device to a second radiation dose that is higher than said first dose to provide a second substantial increase in the cumulative release of said therapeutic agent subsequent to administration to a patient, wherein said second substantial increase is greater than said first substantial increase.

27. A method comprising: (a) identifying an implantable or insertable medical device for which increased release is desired, said implantable or insertable medical device comprising a therapeutic agent and a polymeric release region that further comprises a polymer, and (b) exposing said medical device to a radiation dose that is effective to provide a substantial increase in the cumulative release of said therapeutic agent subsequent to administration to a patient.

28. The implantable or insertable medical device of claim 2, wherein said polymeric release region is treated with a radiation dose in the range of 1 Mrad to 10 M rad.

* * * * *